(12) United States Patent
Druma

(10) Patent No.: US 9,668,796 B2
(45) Date of Patent: Jun. 6, 2017

(54) LOW COST INFLATABLE BONE TAMP

(71) Applicant: KYPHON SARL, Neuchatel (CH)

(72) Inventor: Calin Druma, San Jose, CA (US)

(73) Assignee: Kyphon SÀRL, Neuchatel (CH)

( * ) Notice: Subject to any disclaimer, the term of this patent is extended or adjusted under 35 U.S.C. 154(b) by 0 days.

(21) Appl. No.: 14/856,124

(22) Filed: Sep. 16, 2015

(65) Prior Publication Data

US 2016/0000492 A1 Jan. 7, 2016

Related U.S. Application Data

(63) Continuation of application No. 13/789,127, filed on Mar. 7, 2013, now Pat. No. 9,149,318.

(51) Int. Cl.
*A61B 17/88* (2006.01)

(52) U.S. Cl.
CPC ...... *A61B 17/8855* (2013.01); *A61B 17/8808* (2013.01); *A61B 17/8811* (2013.01); *A61B 17/8819* (2013.01); *A61B 17/8858* (2013.01)

(58) Field of Classification Search
CPC ... A61B 17/88; A61B 17/885; A61B 17/8852; A61B 17/8855; A61B 17/8858; A61B 17/8819
USPC ......... 606/63, 90, 92–94, 99, 105, 191–200; 604/164.01–170.03
See application file for complete search history.

(56) References Cited

U.S. PATENT DOCUMENTS

| | | | |
|---|---|---|---|
| 4,646,742 A * | 3/1987 | Packard | A61M 25/104 604/102.02 |
| 4,884,573 A | 12/1989 | Wijay et al. | |
| 4,969,888 A | 11/1990 | Scholten et al. | |
| 5,304,134 A * | 4/1994 | Kraus | A61M 25/0045 604/102.02 |
| 5,387,193 A * | 2/1995 | Miraki | A61M 25/104 604/102.02 |
| 5,429,597 A | 7/1995 | DeMello et al. | |
| 5,807,330 A * | 9/1998 | Teitelbaum | A61M 25/1018 604/509 |
| 5,827,289 A | 10/1998 | Reiley et al. | |
| 6,648,854 B1 * | 11/2003 | Patterson | A61M 25/005 604/524 |
| 6,656,152 B2 * | 12/2003 | Putz | A61M 25/0662 604/510 |
| 6,673,042 B1 * | 1/2004 | Samson | A61M 29/02 604/104 |
| 6,802,825 B2 * | 10/2004 | Ackerman | A61M 25/10 604/103.03 |

(Continued)

FOREIGN PATENT DOCUMENTS

WO 2006019626 A2 2/2006
WO 2012125184 A1 9/2012

*Primary Examiner* — Christian Sevilla
*Assistant Examiner* — Eric S Gibson

(57) ABSTRACT

A surgical system and method for correction of a bone injury or disorder are provided. The device includes an elongated shaft that extends between a proximal end and a distal end and defining an interior lumen. A valve disposed with the proximal end of the elongated shaft and including a membrane. An inflatable structure is coupled to the distal end of the elongated shaft. A stylet is configured for insertion through the membrane and is removably disposed in the interior lumen of the elongated shaft such that the stylet provides strength to the elongated shaft.

20 Claims, 4 Drawing Sheets

(56) References Cited

U.S. PATENT DOCUMENTS

| | | | |
|---|---|---|---|
| 6,960,188 B2* | 11/2005 | Jorgensen | A61M 25/1006 604/103.09 |
| 7,087,058 B2 | 8/2006 | Cragg | |
| 7,115,137 B2* | 10/2006 | Duchamp | B29C 57/00 604/103 |
| 7,261,720 B2* | 8/2007 | Stevens | A61B 10/025 606/105 |
| 7,722,624 B2* | 5/2010 | Boucher | A61B 17/68 606/105 |
| 7,771,369 B2 | 8/2010 | Griffin et al. | |
| 7,862,541 B2* | 1/2011 | Jeffrey | A61M 25/0069 604/96.01 |
| 7,875,035 B2* | 1/2011 | Boucher | A61B 17/68 606/105 |
| 7,985,228 B2* | 7/2011 | Phan | A61B 17/8855 606/90 |
| 8,277,438 B2 | 10/2012 | Griffin et al. | |
| 8,617,167 B2* | 12/2013 | Weisel | A61B 17/0218 600/201 |
| 8,684,963 B2* | 4/2014 | Qiu | A61M 25/0009 604/96.01 |
| 9,149,318 B2* | 10/2015 | Druma | A61B 17/8855 |
| 2003/0023230 A1* | 1/2003 | Lewis | A61B 17/22 604/537 |
| 2003/0032921 A1* | 2/2003 | Duchamp | A61M 25/1036 604/103 |
| 2003/0050644 A1* | 3/2003 | Boucher | A61B 17/3472 606/90 |
| 2003/0105508 A1 | 6/2003 | Johnson et al. | |
| 2003/0191489 A1 | 10/2003 | Reiley et al. | |
| 2004/0010263 A1* | 1/2004 | Boucher | A61B 17/8855 606/99 |
| 2004/0193108 A1* | 9/2004 | Ackerman | A61M 25/10 604/103.07 |
| 2005/0055043 A1* | 3/2005 | Foltz | A61M 25/1011 606/193 |
| 2005/0234453 A1* | 10/2005 | Shaolian | A61B 17/1671 606/60 |
| 2005/0251140 A1* | 11/2005 | Shaolian | A61B 17/1671 606/60 |
| 2006/0015132 A1* | 1/2006 | Rioux | A61B 17/3462 606/191 |
| 2006/0195115 A1 | 8/2006 | Ferree | |
| 2006/0258987 A1* | 11/2006 | Lentz | A61M 25/0054 604/164.01 |
| 2007/0005092 A1* | 1/2007 | Godin | A61M 25/0023 606/194 |
| 2007/0055300 A1* | 3/2007 | Osorio | A61B 17/1604 606/192 |
| 2007/0208301 A1* | 9/2007 | Evard | A61M 25/10 604/103.1 |
| 2007/0282367 A1* | 12/2007 | Jeffrey | A61F 2/958 606/194 |
| 2008/0051707 A1* | 2/2008 | Phan | A61B 17/8855 604/108 |
| 2008/0058931 A1 | 3/2008 | White et al. | |
| 2008/0065091 A1* | 3/2008 | Scribner | A61B 17/8816 606/94 |
| 2008/0132935 A1* | 6/2008 | Osorio | A61B 17/1604 606/192 |
| 2009/0177200 A1* | 7/2009 | Saab | A61B 17/8855 606/63 |
| 2009/0177206 A1* | 7/2009 | Lozier | A61B 17/1617 606/93 |
| 2009/0299373 A1 | 12/2009 | Sisken | |
| 2009/0299374 A1* | 12/2009 | Tilson | A61B 17/8816 606/94 |
| 2009/0306597 A1* | 12/2009 | Lupton | A61B 17/3207 604/164.13 |
| 2009/0306700 A1 | 12/2009 | Miyata et al. | |
| 2009/0312806 A1* | 12/2009 | Sherman | A61F 2/44 606/86 R |
| 2009/0312807 A1* | 12/2009 | Boudreault | A61B 17/025 606/86 R |
| 2010/0076269 A1* | 3/2010 | Makower | A61B 1/233 600/178 |
| 2010/0179556 A1* | 7/2010 | Scribner | A61B 17/8816 606/80 |
| 2010/0222766 A1* | 9/2010 | Stalker | A61M 25/0041 604/500 |
| 2010/0234876 A1* | 9/2010 | Watson | A61B 18/02 606/194 |
| 2010/0241178 A1* | 9/2010 | Tilson | A61B 17/8816 606/86 R |
| 2010/0262069 A1* | 10/2010 | Rabiner | A61B 17/7097 604/21 |
| 2010/0274246 A1* | 10/2010 | Beyar | A61B 17/7258 606/63 |
| 2011/0098713 A1* | 4/2011 | Rabiner | A61B 17/7097 606/93 |
| 2011/0106184 A1* | 5/2011 | Sapida | A61B 17/8855 606/86 R |
| 2011/0137319 A1* | 6/2011 | Ralph | A61B 17/1686 606/94 |
| 2011/0190831 A1* | 8/2011 | Mafi | A61F 2/958 606/86 R |
| 2011/0202064 A1* | 8/2011 | O'Halloran | A61B 17/7097 606/94 |
| 2011/0264099 A1* | 10/2011 | Quinto | A61B 17/8855 606/94 |
| 2011/0313356 A1* | 12/2011 | Rabiner | A61B 17/7275 604/103.02 |
| 2012/0059317 A1 | 3/2012 | Michiyo et al. | |
| 2012/0071825 A1 | 3/2012 | Cisko, Jr. | |
| 2012/0209176 A1* | 8/2012 | Anderson | A61B 17/3207 604/103.02 |
| 2012/0232570 A1* | 9/2012 | Jenson | A61B 17/3207 606/159 |
| 2012/0259355 A1* | 10/2012 | Druma | A61B 17/8855 606/192 |
| 2012/0259375 A1* | 10/2012 | Druma | A61B 17/8855 606/86 R |
| 2013/0204268 A1* | 8/2013 | Mafi | A61B 17/8855 606/105 |
| 2014/0005711 A1* | 1/2014 | Saab | A61M 25/0144 606/191 |
| 2014/0114325 A1* | 4/2014 | Wu | A61B 17/320725 606/127 |
| 2014/0163467 A1* | 6/2014 | Ramsey, III | A61B 17/12136 604/103.01 |
| 2014/0214085 A1* | 7/2014 | Druma | A61B 17/8855 606/279 |
| 2014/0257311 A1* | 9/2014 | Druma | A61B 17/8855 606/90 |

\* cited by examiner

LOW COST INFLATABLE BONE TAMP

CROSS-REFERENCE TO RELATED APPLICATIONS

This application is a continuation of U.S. patent application Ser. No. 13/789,127, filed Mar. 7, 2013, which is hereby incorporated by reference herein in its entirety.

TECHNICAL FIELD

The present disclosure generally relates to medical devices for the treatment of musculoskeletal structures, and more particularly to a surgical system and method employing a balloon and catheter having a stiffening stylet.

BACKGROUND

Extremity fractures of a calcaneus or other bone may be reduced percutaneously using Inflatable Bone Tamps (IBTs). While effective, IBTs are typically designed for the spine and the lifting of vertebral bodies. The inflation profiles of these balloons are most effective at lifting flat surfaces. However, calcaneus fractures typically occur on the superior, anterior portion of the bone, which normally has an angled orientation. What is needed is an IBT having features that can be used more easily with calcaneus fractures. Such IBT's are provided herein.

SUMMARY

Accordingly, a surgical system and method for correction of a bone injury or disorder are provided. In one embodiment, in accordance with the principles of the present disclosure, a device for performing a surgical procedure. The device includes an elongated shaft that extends between a proximal end and a distal end and defining an interior lumen. A valve disposed with the proximal end of the elongated shaft and including a membrane. An inflatable structure is coupled to the distal end of the elongated shaft. A stylet is configured for insertion through the membrane and is removably disposed in the interior lumen of the elongated shaft such that the stylet provides strength to the elongated shaft.

In one embodiment, a system for performing a surgical procedure is provided. The system includes a cannula defining an access lumen. An elongated shaft that extends between a proximal end and a distal end and defining an interior lumen. A valve is disposed with the proximal end of the elongated shaft and includes a membrane. An inflatable structure is coupled to the distal end of the elongated shaft. A stylet is configured for insertion through the membrane and is removably disposed in the interior lumen of the elongated shaft such that the stylet provides strength to the elongated shaft.

In one embodiment, a method for repairing a bone is provided. The method comprises the steps of: providing a device for a surgical procedure including a cannula defining an access lumen. The device having an elongated shaft extending between a proximal end and a distal end and defining an interior lumen. A valve is disposed with the proximal end of the elongated shaft and includes a membrane. An inflatable structure is coupled to the distal end of the elongated shaft which is used to lift or treat the bone fracture. A stylet configured for insertion through the membrane is provided and is removably disposed in the interior lumen of the elongated shaft such that the stylet provides strength to the elongated shaft. Inserting the cannula into a patient to the site of treatment. Once in position, insert the stylet through the membrane and into the elongated shaft of the device. Positioning the elongated shaft through the cannula and into a boney structure of the patient. Inflating the inflatable structure to treat and/or manipulate bone. Deflating the inflatable structure once treatment is completed and withdrawing the elongated shaft from the patient.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
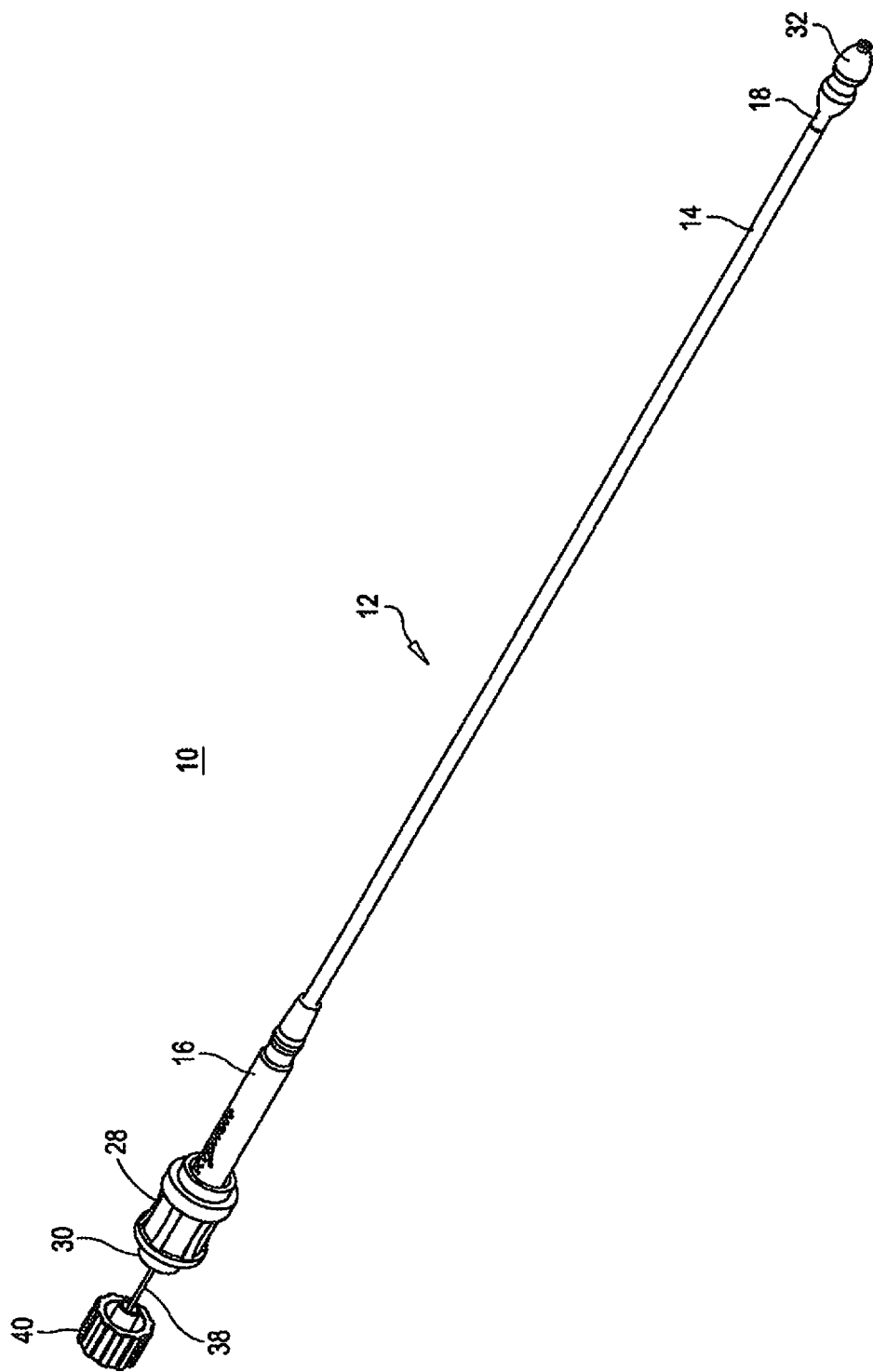
FIG. 1 is a side perspective view of one embodiment of an inflatable balloon system in accordance with the principles of the present disclosure.

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method can include inflatable bone tamps (IBT) presenting an angled surface for the repair of bones.

In one embodiment, the system and method include a low cost IBT including a stiffening stylet. The stylet is provided to add column strength to the elongated shaft. The stylet is inserted into a valve and through a membrane, such as, for example, a silicon gasket disposed with the valve. In one embodiment, the membrane includes a slit configured to receive the stylet. One type of value that can be used is an EZ-prep valve. When the balloon is positioned, the stylet is removed from the IBT and the inflation device is connected to the IBT through the valve. In one embodiment, an adapter is disposed between the elongated shaft and the valve.

In one embodiment, the stylet is "free floating" inside the elongated shaft of the IBT. The stylet is confined between the distal tip of the inflatable structure and the proximal end of the elongated shaft. The inflatable structure is inflated with the stylet in place. The stylet is configured to leave space for inflation of the inflatable structure. For example, the lumen diameter is smaller than the diameter of the free floating stylet allowing room for inflation of the balloon at the distal tip.

It is contemplated that one or all of the components of the surgical system may be disposable, peel-pack, pre-packed sterile devices. One or all of the components of the surgical system may be reusable. The surgical system may be configured as a kit with multiple sized and configured components.

It is envisioned that the present disclosure may be employed to treat bones, and in particular extremity bones such as the calcaneus. It should be understood that the present principles are applicable to any bone structures, including but not limited to bones of the spine, legs, feet, arms, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there are illustrated components of a surgical system, such as, for example, an inflatable balloon system 10 and embodiments in accordance with the principles of the present disclosure.

The components of balloon system 10 can be fabricated from biologically acceptable materials suitable for medical applications, including metals, synthetic polymers, ceramics and bone material and/or their composites, depending on the particular application and/or preference of a medical practitioner. For example, the components of balloon system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), nylon, stiff nylon or other high stiffness polymers, ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of balloon system 10 may have material composites, including the above materials, to achieve various desired characteristics such as strength, rigidity, elasticity, compliance, biomechanical performance, durability and radiolucency or imaging preference. The components of balloon system 10, individually or collectively, may also be fabricated from a heterogeneous material such as a combination of two or more of the above-described materials. The components of balloon system 10 may be monolithically formed, integrally connected or include fastening elements and/or instruments, as described herein.

FIGS. 1-4 show an embodiment of a balloon system 10 that includes an inflatable bone tamp device 12. Device 12 includes an elongated shaft, such as, for example, a catheter 14. Catheter 14 extends between a proximal end 16 and a distal end 18. As shown, catheter 14 is substantially circular but can be variously configured, such as, for example, oval, oblong, triangular, square, polygonal, irregular, uniform, non-uniform and/or tapered. Catheter 14 defines an interior lumen 20. Lumen 20 defines a passageway 22 configured to receive a stylet 38, as discussed herein. Catheter 14 can have a uniform diameter or in one embodiment includes a primary region 24 and a secondary region 26. Region 24 includes a first diameter d1 and region 26 includes a second diameter d2. In one embodiment, d2 is a reduced diameter and is less than d1. In an alternate embodiment, it is contemplated that d1 is less than d2 or d1 is equal to d2. Region 24 transitions to region 26 via a transition region t1. The change is diameter from d1 to d2 occurs along region t1. Catheter 14 can be formed from various materials as stated above, such as, for example, silicone, polyvinyl chloride, latex rubber, polyethylene, polyurethane, Nitinol, polyamide, or stainless steel (or a blend of these materials).

Device 12 includes a valve 28. Valve 28 is disposed with end 16 of catheter 14. Valve is configured to receive components of the system 10, such as, for example, an inflation device (not shown). Valve 28 includes a membrane 30 being constructed from a resealable material, such as, for example, a silicone gasket. Valve 28 is configured to receive stylet 38 through membrane 30. In one embodiment, membrane 30 includes an opening, such as, for example, a slit 31 to receive stylet 38.

Figure 4:
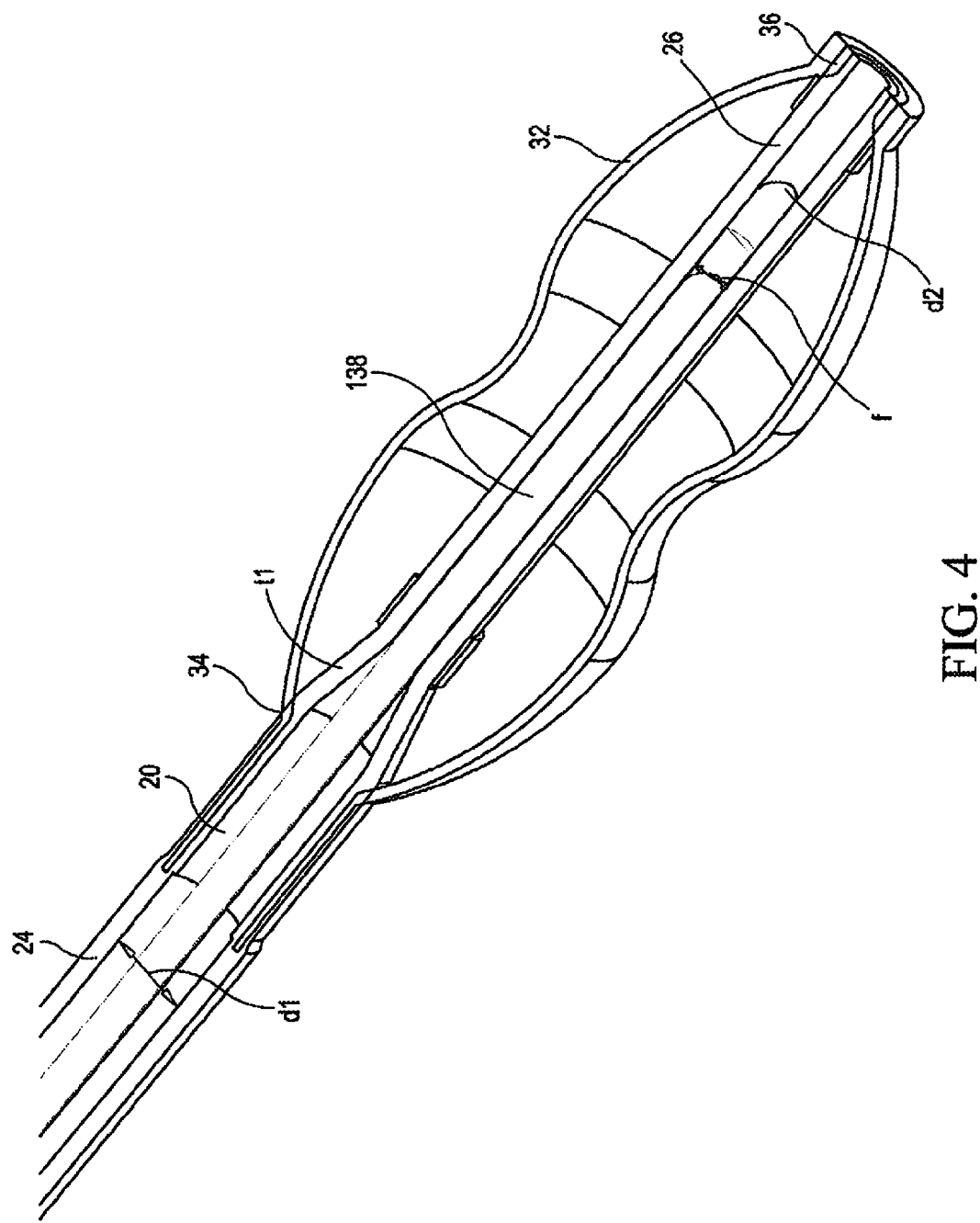
FIG. 4 is perspective cross sectional view of components of the system shown in FIG. 1.

Device 12 includes an inflatable structure, such as, for example, a balloon 32. Balloon 32 extends between a proximal end 34 and a distal end 36. End 36 of balloon 32 is coupled to region 26, such that at least a portion of reduced diameter region d2 is enclosed within balloon 32. As shown in FIG. 4, end 34 of balloon 32 is coupled to region 24 of catheter 14, although other configurations are contemplated such as, for example end 34 is coupled to region t1. Balloon 32 is in communication with lumen 20 such that inflation material flows through lumen 20 to inflate balloon 32. In one embodiment, as shown in FIG. 4, distal end of catheter 14 is open to allow, not encased within balloon 32, for dispensing of a material from the catheter. In one embodiment, catheter 14 includes a port (not shown) continuous with interior lumen 20 such that material can be delivered to balloon 32.

Device 12 includes a stylet 38. Stylet 38 is configured to add support and stiffen catheter 14. Stylet 38 can be constructed of various materials, such as, for example, stainless steel, Nitinol, stiff nylon, or other polymers having a predetermined stiffness, or any other supportive material. Stylet 38 is configured for insertion through membrane 30. Stylet 38 is removably inserted into lumen 20 of catheter 14 to provide some additional rigidity to catheter 14 such as, for example, at region 26 and/or balloon 32 such as, for example, to assist with placement, inflation, and/or removal of device 12 during a surgical procedure. Stylet 38 includes a length such that stylet 38 extends the entire length of catheter and into balloon 32. In one embodiment, as shown in FIG. 1, Stylet 38 includes a cap 40. Cap 40 is configured to secure stylet 38 to valve 28 when stylet 38 is disposed within lumen 20. Cap 40 can engage valve 28 via a threaded connection or a locking interface. In one embodiment the proximal end of the stylet 38 is connected to cap 40 and can be removed by unlocking the cap 40 and pulling the stylet 38 out of the sealed catheter 14.

In one embodiment, a device similar to device 12 described above is shown in FIGS. 3-4. In this embodiment, stylet 138 is a length such that it is moveable within lumen 20, i.e., is free floating within the lumen. That is, the diameter f of stylet 138 is smaller than the diameter of the lumen 20. In this configuration, stylet 138 remains within catheter 14 during inflation of balloon 32 and is moveable to allow inflation material to pass into balloon 32. Once stylet 138 is inserted through membrane 30, membrane 30 reseals itself.

In assembly, operation and use, system 10 is employed with a surgical procedure, such as, for a correction or treatment of bone fractures. It is contemplated that one or all of the components of system 10 can be delivered or implanted as a pre-assembled device or can be assembled in situ. System 10 may be completely or partially revised, removed or replaced as part of the operation.

Figure 2:
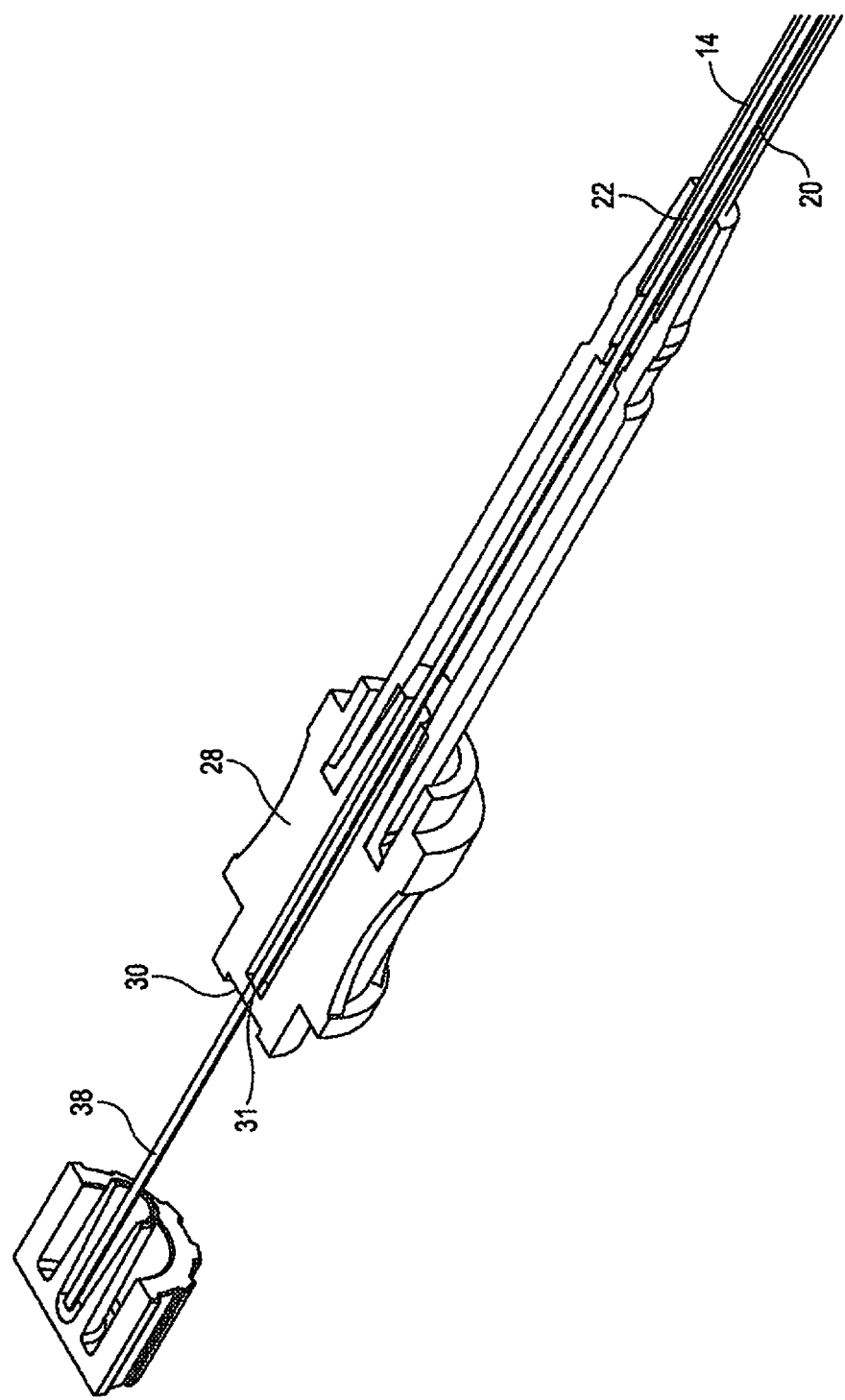
FIG. 2 is perspective cross sectional view of components of the system shown in FIG. 1.
Figure 3:
FIG. 3 is a cross sectional view of one embodiment of an inflatable balloon system in accordance with the principles of the present disclosure.

For example, as shown in FIGS. 1-2, system 10, described above, can be employed with a surgical correction treatment of an applicable condition or injury of an affected portion of a, calcaneus bone, bones of the feet or hands, bones of the spine, bones of the arms and legs, etc. and other areas within a body. The balloon can also be used to distract joints for ligament repair or distract soft tissue.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 10 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 10 is determined according to the configuration, dimension and location of a selected section of the bone fracture and the requirements of a particular application.

An incision is made in the body of a patient and a cutting instrument (not shown) creates a surgical pathway for implantation of components of system 10. This may include the use of a cannula or other device. A preparation instrument (not shown) can be employed to prepare tissue surfaces, as well as for aspiration and irrigation of a surgical region according to the requirements of a particular surgical application.

Device 12, as described above, is provided. A cannula (not shown) is inserted into the patient along the surgical pathway. Stylet 38 is inserted through membrane 30 of valve 28 into catheter 14. Catheter 14 is placed into the cannula and positioned with the patient at the surgical site, such as, for example, at a boney structure. Catheter 14 is manipulated and maintains its stiffness via stylet 38. Once catheter 14 is positioned, stylet 38 is removed and membrane 30 reseals itself at the area where stylet 38 was inserted. An inflation device (not shown) can be attached to valve to inflate balloon 32. Balloon 32 is configured to compress cancellous bone to create a cavity or created space within a boney structure or to reposition bone fractures to the proper alignment. When the desired placement of the bone or cavity is created, balloon 32 is deflated and device 12 is removed from the patient. Bone filler material may be added using a separate device. In one embodiment where the catheter is stiff enough for insertion, the catheter can be positioned first and then the stylet added.

Other components of system 10 may delivered to the surgical site along the surgical pathway(s). In one embodiment, system 10 includes an agent, which may be disposed, packed or layered within, on or about the components and/or surfaces of system 10. It is envisioned that the agent may include bone growth promoting material, such as, for example, bone graft to enhance fixation of the fixation elements with the bone in need of repair.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 10 can be made of radiolucent materials such as polymers. Radiomarkers may be included for identification under x-ray, fluoroscopy, CT or other imaging techniques. For example, the tip of the stylet can be used as a visualization marker replacing the distal marker band. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair spinal deterioration or damage, with the aid of system 10. Upon completion of the procedure, the surgical instruments and assemblies are removed. The opening drilled in to the bone is filled with a bone cement to provide support for the repaired bone, and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The balloon can be modified or extended to accommodate particular formulations of balloon construction materials or fabrication techniques. Different balloon materials and surface coatings, or outer layers of different materials or surface coatings may also be applied to the balloon to facilitate a smaller balloon profile, biocompatibility, lubrication as well as other properties. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A balloon catheter comprising:
a catheter extending between opposite proximal and distal ends, the catheter comprising an inner surface defining a lumen, the distal end comprising an opening that is in communication with the lumen, the proximal end comprising a valve, the valve including a membrane;
a balloon having a distal end coupled to the distal end of the catheter such that a distal end surface of the balloon is flush with a distal end surface of the catheter; and
a stylet extending through the membrane such that the stylet is removably disposed in the lumen to provide strength to the catheter, the stylet having a length that prevents a distal tip of the stylet from being positioned distal to the distal end surface of the balloon,
wherein the stylet has a maximum diameter that is less than that of the lumen and the opening such that a material in the lumen may be passed around the stylet and exit the lumen through the opening.

2. A balloon catheter as recited in claim 1, wherein the lumen is in communication with an interior volume of the balloon.

3. A balloon catheter as recited in claim 1, wherein the catheter comprises a port that is continuous with the lumen such that a material can be moved through the port and into an interior volume of the balloon to inflate the balloon.

4. A balloon catheter as recited in claim 1, wherein the stylet remains within the catheter during inflation of the balloon and is moveable to allow inflation material to pass into the balloon.

5. A balloon catheter as recited in claim 1, wherein the catheter comprises a primary region having a first diameter and a secondary region having a second diameter, the first diameter being greater than the second diameter, the stylet being configured to be positioned within the secondary region.

6. A balloon catheter as recited in claim 5, wherein a proximal end of the balloon is coupled to the primary region and a distal end of the balloon is coupled to the secondary region.

7. A balloon catheter as recited in claim 5, wherein:
the catheter comprises a transition region that is continuously tapered from the primary region to the secondary region; and
a proximal end of the balloon is coupled to the transition region and a distal end of the balloon is coupled to the secondary region.

8. A balloon catheter as recited in claim 1, wherein the stylet includes a length such that the stylet extends an entire length of the catheter and into a portion of the catheter that is surrounded by the balloon.

9. A balloon catheter as recited in claim 1, wherein the catheter has a uniform diameter.

10. A balloon catheter as recited in claim 1, wherein the stylet is confined between a distal tip of the balloon and the proximal end.

11. A balloon catheter as recited in claim 1, wherein the catheter comprises a flexible material and the stylet comprises a rigid material.

12. A balloon catheter as recited in claim 1, wherein the catheter comprises a material selected from a group consisting of silicone, polyvinyl chloride, and latex rubber and the stylet comprises a material selected from a group consisting of stainless steel, Nitinol, and stiff nylon.

13. A balloon catheter as recited in claim 1, wherein a distal end of the stylet comprises a blunt tip.

14. A balloon catheter comprising:
a catheter extending between opposite proximal and distal ends, the catheter comprising an inner surface defining a lumen, the distal end comprising an opening that is in communication with the lumen, the proximal end comprising a valve, the valve including a membrane constructed from a resealable material;
a balloon comprising a distal end that is coupled to the distal end of the catheter such that a distal end surface of the balloon is flush with a distal end surface of the catheter; and a stylet extending through the membrane such that the stylet is removably disposed in the lumen to provide strength to the catheter, the stylet having a length that prevents a distal tip of the stylet from being positioned distal to the distal end surface of the balloon, wherein the catheter comprises a port that is continuous with the lumen such that a material can be moved through the port and into an interior volume of the balloon to inflate the balloon, wherein the stylet has a maximum diameter that is less than that of the lumen and the opening such that a material in the lumen may be passed around the stylet and exit the lumen through the opening.

15. A method comprising:

inserting a cannula into a patient;

inserting a catheter through the cannula such that a balloon is positioned within the patient, a distal end of the balloon being coupled to a distal end of the catheter such that a distal end surface of the balloon is flush with a distal end surface of the catheter, the catheter comprising an inner surface defining a lumen, the distal end of the catheter comprising an opening that is in communication with the lumen, the catheter further comprising a port that is continuous with the lumen, wherein a proximal end of the catheter comprises a valve, the valve including a membrane;

inserting a stylet through the membrane such that the stylet is removably disposed in the lumen to provide strength to the catheter, the stylet has a maximum diameter that is less than that of the lumen and the opening, the stylet having a length that prevents a distal tip of the stylet from being positioned distal to the distal end surface of the balloon;

moving a material through the lumen and around the stylet such that the material exits the lumen through the opening and moves into the boney structure; and withdrawing the catheter from the patient.

16. A method as recited in claim 15, wherein the stylet extends through the membrane and into the lumen.

17. A method as recited in claim 15, further comprising inflating the balloon and deflating the balloon.

18. A method as recited in claim 15, wherein the stylet extends through the membrane and into the lumen while the material moves through the lumen and the opening and into the boney structure.

19. A method as recited in claim 15, wherein the membrane reseals itself once the stylet is inserted through the membrane.

20. A method as recited in claim 15, further comprising removing the stylet from the catheter after the balloon is positioned in the boney structure.

\* \* \* \* \*